US010861417B2

(12) United States Patent
Gollier et al.

(10) Patent No.: US 10,861,417 B2
(45) Date of Patent: Dec. 8, 2020

(54) HEAD MOUNTED DISPLAY WITH WIDE FIELD OF VIEW AND INSET DISPLAY

(71) Applicant: Facebook Technologies, LLC, Menlo Park, CA (US)

(72) Inventors: Jaques Gollier, Bellevue, WA (US); Brian Wheelwright, Sammamish, WA (US); Barry David Silverstein, Kirkland, WA (US)

(73) Assignee: Facebook Technologies, LLC, Menlo Park, CA (US)

( * ) Notice: Subject to any disclaimer, the term of this patent is extended or adjusted under 35 U.S.C. 154(b) by 0 days.

(21) Appl. No.: 16/287,785

(22) Filed: Feb. 27, 2019

(65) Prior Publication Data
US 2020/0273426 A1    Aug. 27, 2020

(51) Int. Cl.
| | | |
|---|---|---|
| *G06F 3/01* | (2006.01) |
| *H04N 9/31* | (2006.01) |
| *G02B 27/00* | (2006.01) |
| *G02B 27/30* | (2006.01) |
| *H04N 13/332* | (2018.01) |
| *G09G 5/10* | (2006.01) |
| *G06T 5/10* | (2006.01) |
| *G06T 7/20* | (2017.01) |

(52) U.S. Cl.
CPC ............ *G09G 5/10* (2013.01); *G02B 27/0081* (2013.01); *G02B 27/0093* (2013.01); *G02B 27/30* (2013.01); *G06F 3/013* (2013.01); *G06T 5/10* (2013.01); *H04N 9/3102* (2013.01); *A61M 2205/507* (2013.01); *G06T 7/20* (2013.01); *G09G 2300/023* (2013.01); *G09G 2320/068* (2013.01); *G09G 2320/0613* (2013.01); *G09G 2340/0407* (2013.01); *G09G 2354/00* (2013.01); *H04N 13/332* (2018.05)

(58) Field of Classification Search
CPC .............. G09G 5/10; G09G 2320/068; G09G 2320/0613; G09G 2354/00; G09G 2340/0407; G09G 2300/023; G06F 3/013; G06T 5/10; G06T 7/20; G02B 27/0081; G02B 27/30; G02B 27/0093; H04N 9/3102; H04N 13/322; A61M 2205/507
See application file for complete search history.

(56) References Cited

U.S. PATENT DOCUMENTS

| | | | | |
|---|---|---|---|---|
| 6,043,799 A | * | 3/2000 | Tidwell ................. | G02B 7/287 345/7 |
| 2014/0362180 A1 | * | 12/2014 | Bickerstaff ........ | G02B 27/0172 348/43 |
| 2016/0370855 A1 | * | 12/2016 | Lanier ..................... | G06F 3/005 |

* cited by examiner

*Primary Examiner* — Brent D Castiaux
(74) *Attorney, Agent, or Firm* — Freestone Intellectual Property Law PLLC; Aaron J. Visbeek (57) ABSTRACT

Display having a wide field of view is provided. A transparent display provides inset display light having a field of view narrower than the wide field of view. At least a portion of the display light propagates through the transparent display before becoming incident on an eye of the user of an HMD.

19 Claims, 13 Drawing Sheets

HEAD MOUNTED DISPLAY WITH WIDE FIELD OF VIEW AND INSET DISPLAY

TECHNICAL FIELD

This disclosure relates generally to displays, and in particular to wide field of view head mounted displays.

BACKGROUND INFORMATION

Conventional Virtual Reality headsets typically include a focusing lens and a display such as a liquid crystal display (LCD) or an organic light emitting diode (OLED) display. The field of view (FOV) of conventional head mounted displays are about 90-100 degrees horizontal. However, as the FOV expands, display resolution is often sacrificed as a smaller pixel pitch for the display pixels is needed to keep the same resolution.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Embodiments of a system, device, and method for providing a wide field of view with high resolution inset display light are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The systems, devices, and methods for providing a wide field of view with inset display light described in this disclosure include a head mounted display (HMD) with a non-transparent display to provide wide field of view (FOV) display light and a transparent display that provides higher resolution inset display light in a narrower field of view. The transparent display may include a lightguide that directs the inset display light to an eyebox area and some of the display light may propagate through the lightguide before becoming incident on an eye of the user. Using a combination of the non-transparent display and the transparent display allows for a wide field of view with a higher resolution inset display light. The higher resolution inset display light may provide retinal resolution (e.g. approximately 1 arcminute) in the middle of the field of view where the user will spend a majority of time gazing. Furthermore, the higher resolution inset display light provides an appropriate resolution for task-based content for productivity contexts (e.g. reading text and documents). In some embodiments of the disclosure, the transparent display may be switched on and off depending on different use cases. These and other embodiments are described with respect to FIGS. 1-11.

Figure 1:
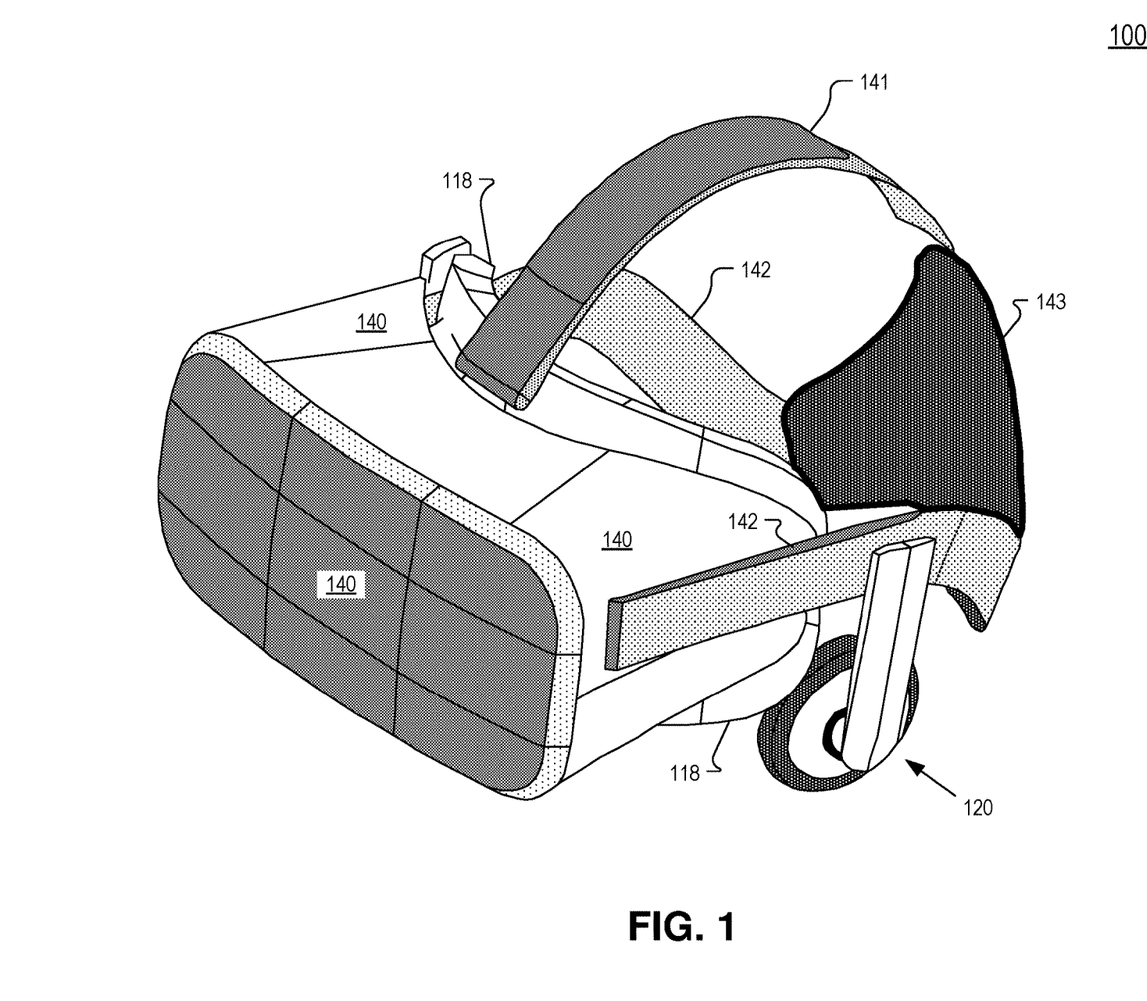
FIG. 1 illustrates an example head mounted display (HMD) that may include a non-transparent display emitting wide field of view display light and a transparent display generating inset display light, in accordance with an embodiment of the disclosure.

FIG. 1 illustrates an example head mounted display (HMD) 100 that may include a non-transparent display emitting wide FOV display light and a transparent display generating inset display light, in accordance with an embodiment of the disclosure. Example head mounted display (HMD) 100 includes a top structure 141, a rear securing structure 143, and a side structure 142 attached with a viewing structure 140 having a front rigid body. The illustrated HMD 100 is configured to be worn on a head of a user of the HMD. In one embodiment, top structure 141 includes a fabric strap that may include elastic. Side structure 142 and rear securing structure 143 may include a fabric as well as rigid structures (e.g. plastics) for securing the HMD to the head of the user. HMD 100 may optionally include earpiece (s) 120 configured to deliver audio to the ear(s) of a wearer of HMD 100.

In the illustrated embodiment, viewing structure 140 includes an interface membrane 118 for contacting a face of a wearer of HMD 100. Interface membrane 118 may function to block out some or all ambient light from reaching the eyes of the wearer of HMD 100.

Example HMD 100 also includes a chassis for supporting hardware of the viewing structure 140 of HMD 100. Hardware of viewing structure 140 may include any of processing logic, wired and/or wireless data interface for sending and receiving data, graphic processors, and one or more memories for storing data and computer-executable instructions. In one embodiment, viewing structure 140 may be configured to receive wired power. In one embodiment, viewing structure 140 is configured to be powered by one or more batteries. In one embodiment, viewing structure 140 may be configured to receive wired data including video data. In one embodiment, viewing structure 140 is configured to receive wireless data including video data.

Viewing structure 140 may include a display and corresponding optical assembly for directing display light to a wearer of HMD 100. The display may include a Liquid Crystal Display (LCD) having a two-dimensional display pixel array of liquid crystal pixels arranged in rows and columns, for example. The display may include an organic light emitting diode (OLED) display, micro-LED display, or quantum dot display for directing display light to a wearer of HMD 100. Viewing structure 140 also includes a transparent display that generates inset display light.

Figure 2:
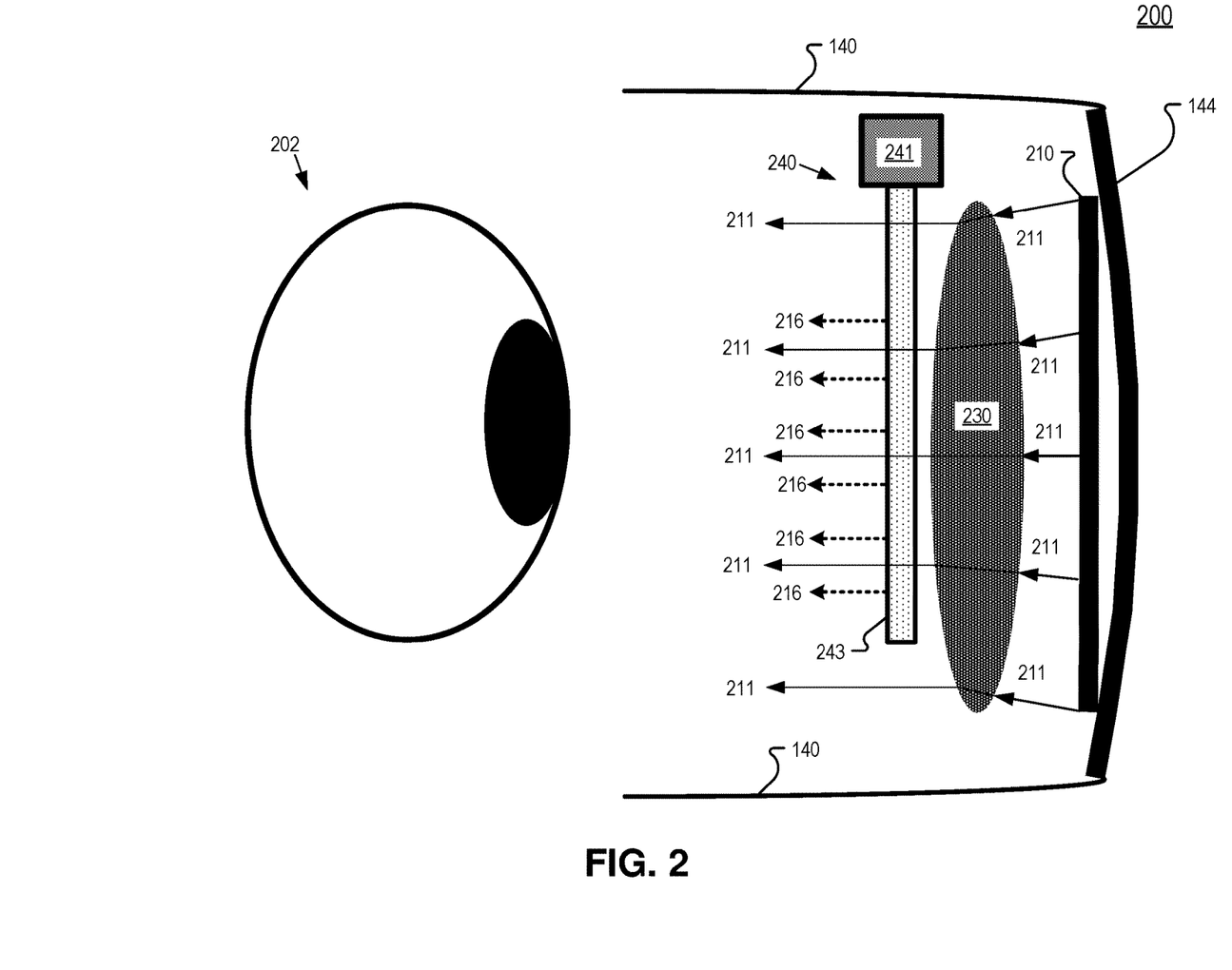
FIG. 2 illustrates a side view of a system including a non-transparent display, an optical assembly, and a transparent display, in accordance with an embodiment of the disclosure.

FIG. 2 illustrates a side view of system 200 including a non-transparent display 210, an optical assembly 230, and a transparent display, in accordance with an embodiment of the disclosure. System 200 may be incorporated into HMD 100, for example. Non-transparent display 210 includes a display pixel array configured to generate display light 211 that may include images for presentation to eye 202. Non-transparent display 210 may include an LCD, OLED display, micro-LED display, or quantum dot display having a two-dimensional display pixel array arranged in rows and columns, for example. Optical assembly 230 may include a double meniscus refractive lens, a Fresnel lens, or a pancake lens, for example. Optical assembly 230 may have an effective focal length of between 20 mm and 30 mm, in some embodiments. Optical assembly 230 may be a collimating lens configured to provide display light 211 to user of an HMD in a wide FOV. In one embodiment, the wide FOV exceeds 100 degrees horizontal. In one embodiment, display light 211 has a wide FOV provided by optical assembly 230 that approaches 200 degrees peripheral vision.

In FIG. 2, transparent display 240 includes a lightguide 243 that directs inset display light 216 to the eye 202 of the user. The inset display light 216 provides a narrower FOV than the wide FOV of display light 211, however transparent display 240 is a higher resolution display than display 210. The narrower FOV provided by inset display light 216 may be in the middle of the wider FOV of display light 211. In other embodiments, the narrower FOV may be in an upper portion, a lower portion, or a side portion of the wider FOV provided by display light 211. In some embodiments the narrower FOV with inset display light may be present in only one eye. The narrower FOV may be 50 degrees horizontal or greater. In FIG. 2, a projector module 241 projects the inset display light into lightguide 243. In one embodiment, projector module 241 includes a liquid crystal on silicon (LCOS) projector. FIG. 2 shows that at least a portion of display light 211 propagates through transparent display 240 before becoming incident on eye 202 of a user of an HMD. In the illustrated embodiment, optical assembly 230 is disposed between lightguide 243 and display 210 and display light 211 propagates through the optical assembly 230 and then through lightguide 243 before becoming incident on eye 202. Although FIG. 2 only illustrates one eye 202, an HMD may have a display 210 (or a portion of a shared display) and an optical assembly 230 for each eye of the user of the HMD.

Figure 3:
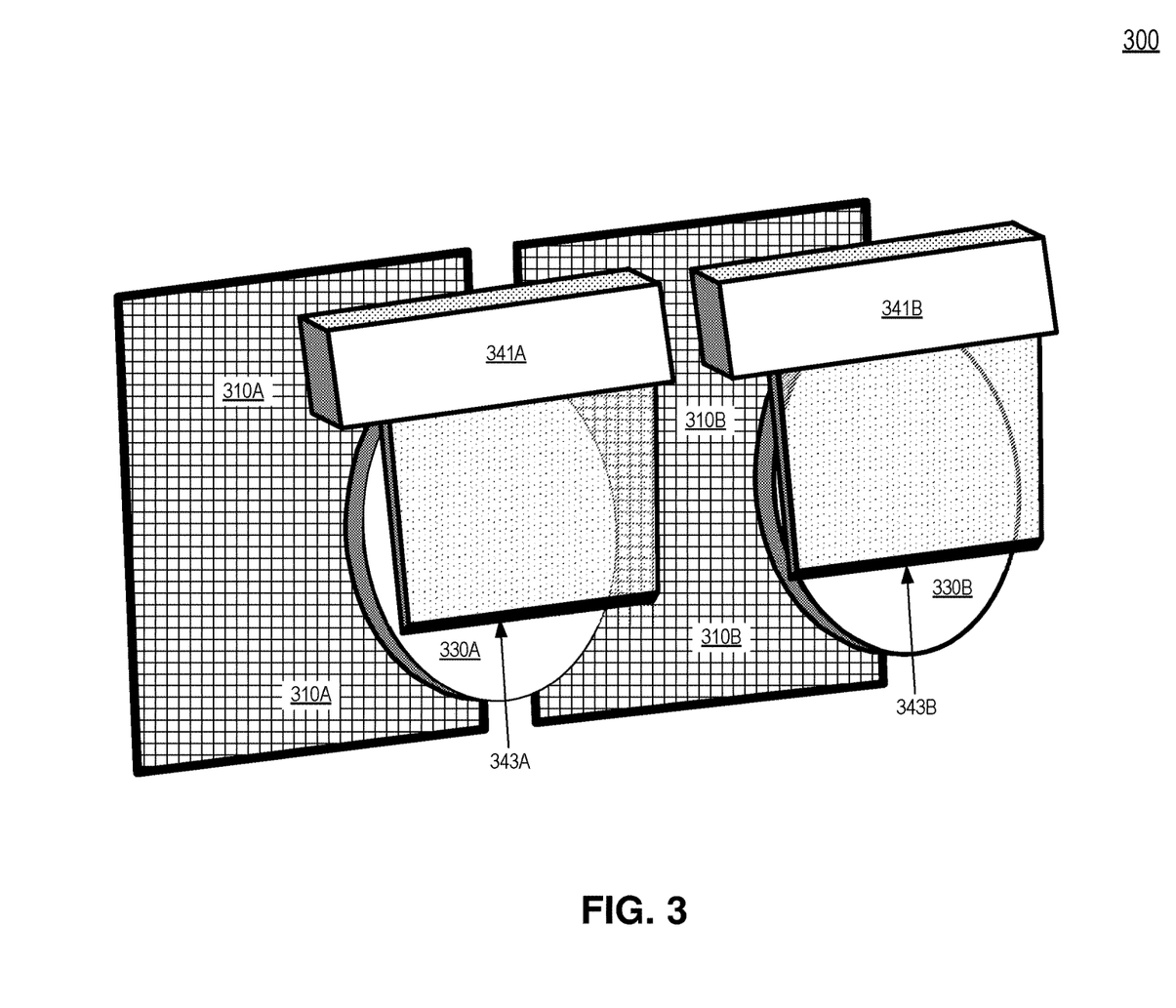
FIG. 3 illustrates a perspective view of example system that includes a non-transparent display, optical assembly, and a transparent display for each eye, in accordance with an embodiment of the disclosure.

FIG. 3 illustrates a perspective view of example system 300 that includes a non-transparent display, optical assembly, and a transparent display for each eye, in accordance with an embodiment of the disclosure. In FIG. 3, displays 310A and 310B are separate displays for each eye. Displays 310 may include the features described with respect to display 210. Displays 310 are shaped as squares in the illustrated embodiment although they may be shaped as rectangles, hexagons or octagons in some embodiments. Similarly, the transparent displays (combination of projector module 341 and lightguide 343 in FIG. 3) may have the features of transparent display 240. In FIG. 3, optical assembly 330A is disposed between non-transparent display 310A and lightguide 343A and optical assembly 330B is disposed between non-transparent display 310B and lightguide 343B.

Figure 4:
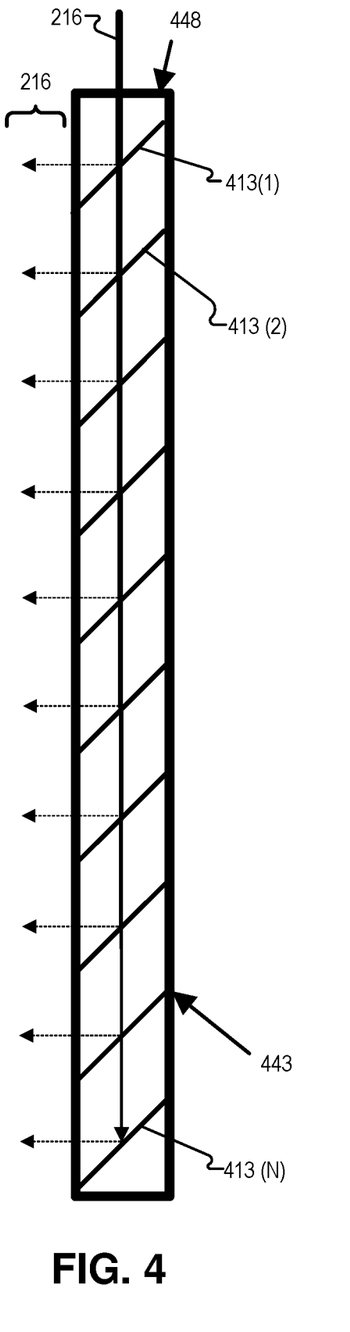
FIG. 4 is a diagram illustration of an example lightguide optic, in accordance with an embodiment of the disclosure.

FIG. 4 is a diagram illustration of a lightguide optic 443 that may be used as lightguide optic 243/343, in accordance with embodiments of the disclosure. Lightguide optic 443 is configured to receive inset display light 216 at a receiving end 448 of the lightguide optic 443. The inset display light 216 may be received from projector module 241, for example. FIG. 4 illustrates that lightguide optic 443 includes a plurality of partially mirrored surfaces 413 configured to redirect inset display light 216 in an eyeward direction. The partially mirrored surfaces 413 are progressively more reflective as a position of the partially mirrored surface gets farther from the receiving end 448 of the lightguide optic 443. The number N of partially mirrored surfaces is equal to ten in the diagram of FIG. 4, although N may be any number in different embodiments. The number N may be much larger or smaller than ten. Partially mirrored surface 413(N) is the last partially mirrored surface while 413(1) is the first partially mirrored surface, in FIG. 4. Partially mirrored surface 413(1) is the partially mirrored surface first encountered by inset display light 216. Since each partially mirrored surface reflects (and redirects) a portion of inset display light 216 to an eyebox area, the intensity of inset display light 216 progressively decreases as it propagates through lightguide optic 443 and encounters the partially mirrored surfaces 413. The width of the illustrated vector representing inset display light 216 within lightguide 443 decreases in FIG. 4 as it propagates through lightguide optic 433 to indicate its decreasing intensity.

In one embodiment, the partially mirrored surface 413(1) reflects less than 10% of inset display light 216 and the last partially reflective surface 413(N) is a mirror that approaches 50% reflectivity. Since the portion of inset display light 216 that encounters last partially mirrored surface 413(N) will have already propagated through partially mirrored surfaces 413(1), 413(2) . . . 413(N−1), the intensity of the inset display light 216 received by last partially mirrored surface 413(N) will be diminished compared to the intensity of the inset display light 216 received by partially mirrored surface 413(1). The reflectivity of each partially mirrored surface between feature 413(1) and 413(N) may progressively increase so that the inset display light 216 (propagating in an eyeward direction) is of substantially uniform intensity across the eyebox area. Since the partially mirrored surfaces are partially reflective, display light 211 will still reach eye 202.

Figure 5:
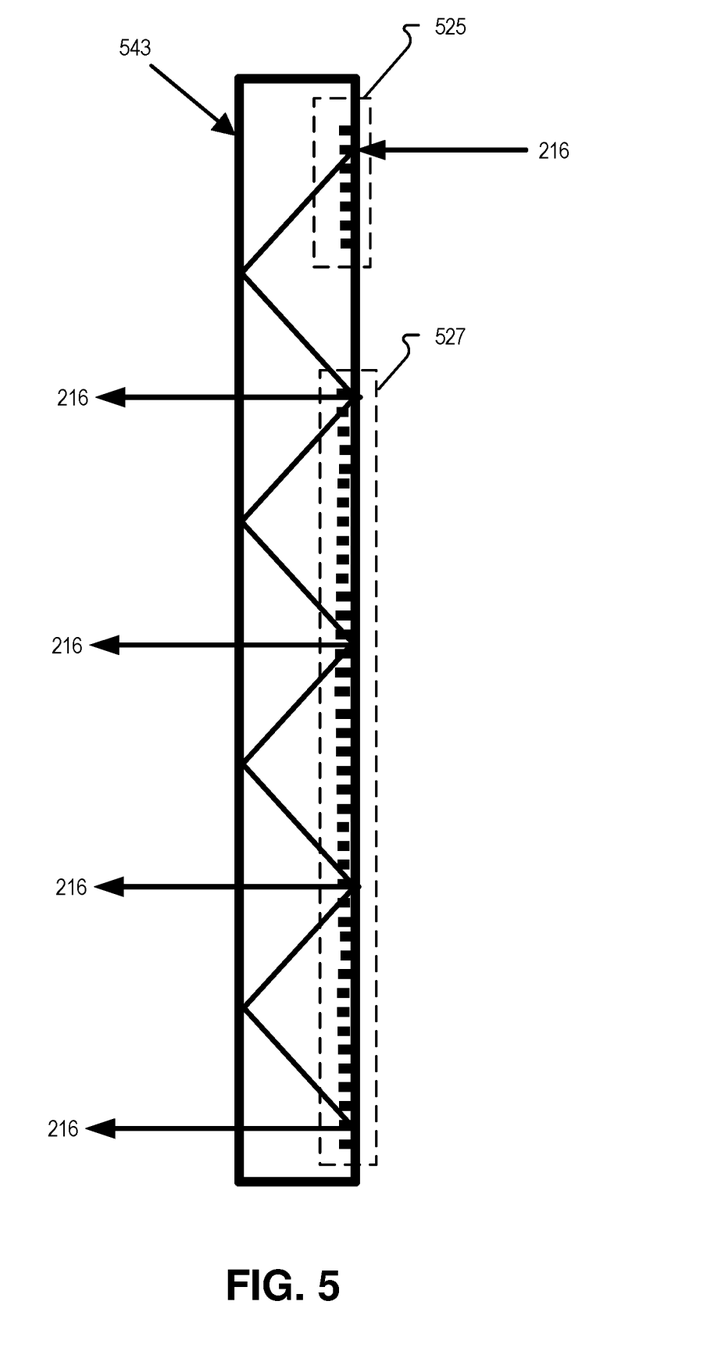
FIG. 5 is a diagram illustration of an example lightguide optic that includes diffractive structures, in accordance with an embodiment of the disclosure.

FIG. 5 is a diagram illustration of a lightguide optic 543 that includes diffractive structures that may be used as lightguide optic 243/343, in accordance with embodiments of the disclosure. Lightguide 543 is configured to incouple inset display light 216 into lightguide optic 543 with incoupling diffraction structure 525. The inset display light 216 may be received from projector module 241, for example. Diffractive structure 525 may be implemented with a surface relief grating or a volumetric Bragg grating, for example.

Inset display light 216 is confined by, and propagates down, lightguide optic 543 except where outcoupling diffractive structure 527 outcouples inset display light 216 and directs in an eyeward direction to an eyebox area. Diffractive structure 527 may be implemented with a surface relief grating or a volumetric Bragg grating, for example. In the illustrated embodiment, the structures 525 and 527 are depicted on a side of lightguide 543 that is opposite of the eye-side, but the structures 525 and 527 may also be disposed on the eye-side of lightguide 543. Similarly, the incoupling structures 525 may also operate in reflection or in transmission (as illustrated). Since the diffractive structure 525 and 527 may be angular and/or wavelength selective, display light 211 may propagate through diffractive structures 525 and 527 with little or no adverse effect.

In conventional Augmented Reality (AR) HMDs, the illumination of diffractive structures by bright light sources (e.g. the sun) cause unacceptable light artifacts that are noticed by users. Many users report seeing bright rainbow images as a result of the scattering by diffractive structures, for example. To address this, conventional lightguide designers have included addition mitigation features to blunt these undesirable scattering effects. However, the mitigation features are often more complex and expensive to manufacture. Notably, embodiments of the disclosure utilize diffraction structure in lightguide optics that may be blocked from exposure to extremely bright light sources (e.g. direct room lighting and the sun) by way of the enclosing virtual reality form factor illustrated in FIG. 1, for example. Consequently, embodiments of the disclosure may utilize lightguides that do not include the more complex and expensive mitigation features and thus save on cost without generating undesirable and noticeable visual artifacts.

Figure 6A:
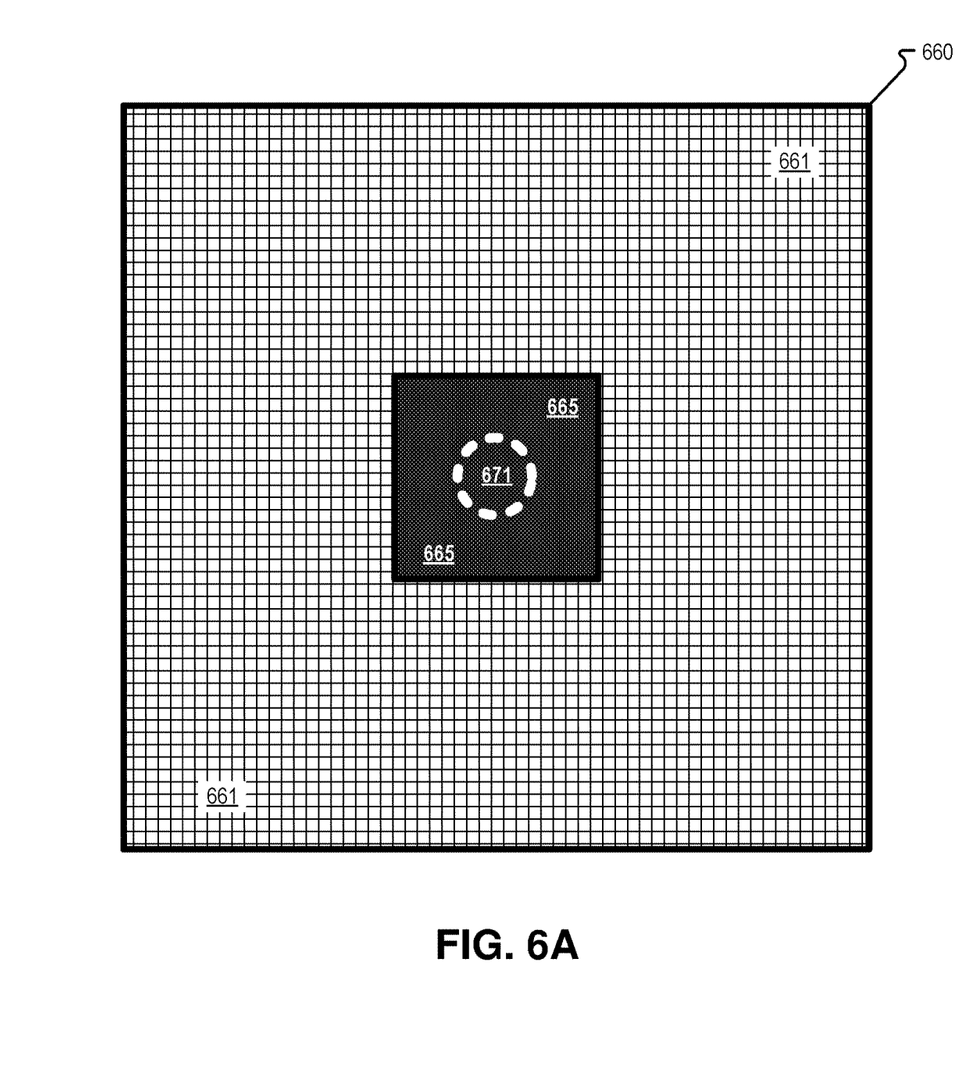
FIGS. 6A-6C illustrate a camera disposed in a pixel void region of a display pixel array, in accordance with an embodiment of the disclosure.

FIG. 6A illustrates a front view of an example non-transparent display 660 having display pixel array 661 including a pixel void region 665, in accordance with an embodiment of the disclosure. Pixel void region 665 is surrounded by display pixels of non-transparent display pixel array 661, in FIG. 6A. The non-transparent display pixel array 661 may be included in display 210, for example. Pixel void region 665 does not have display pixels in it or the display pixel are not driven to emit display light 211. Pixel void region 665 is in a portion of the wide FOV that is illuminated by inset display light 216. Consequently, the inset display light 216 in the narrower field of view fills the portion of the FOV of the user that would otherwise be illuminated by display light from display pixels if there were display pixels in pixel void region 665.

In FIG. 6A, a camera 671 is disposed in the pixel void region 665. Since inset display light 216 may illuminate an inset field of view of the user that is in the middle of the wide FOV provided by display light 211, the two-dimensional footprint that would otherwise include display pixels can be utilized for other components. In the illustrated embodiment, a camera (which may include a lens and CMOS image sensor) is disposed in the pixel void region.

Figure 6B:
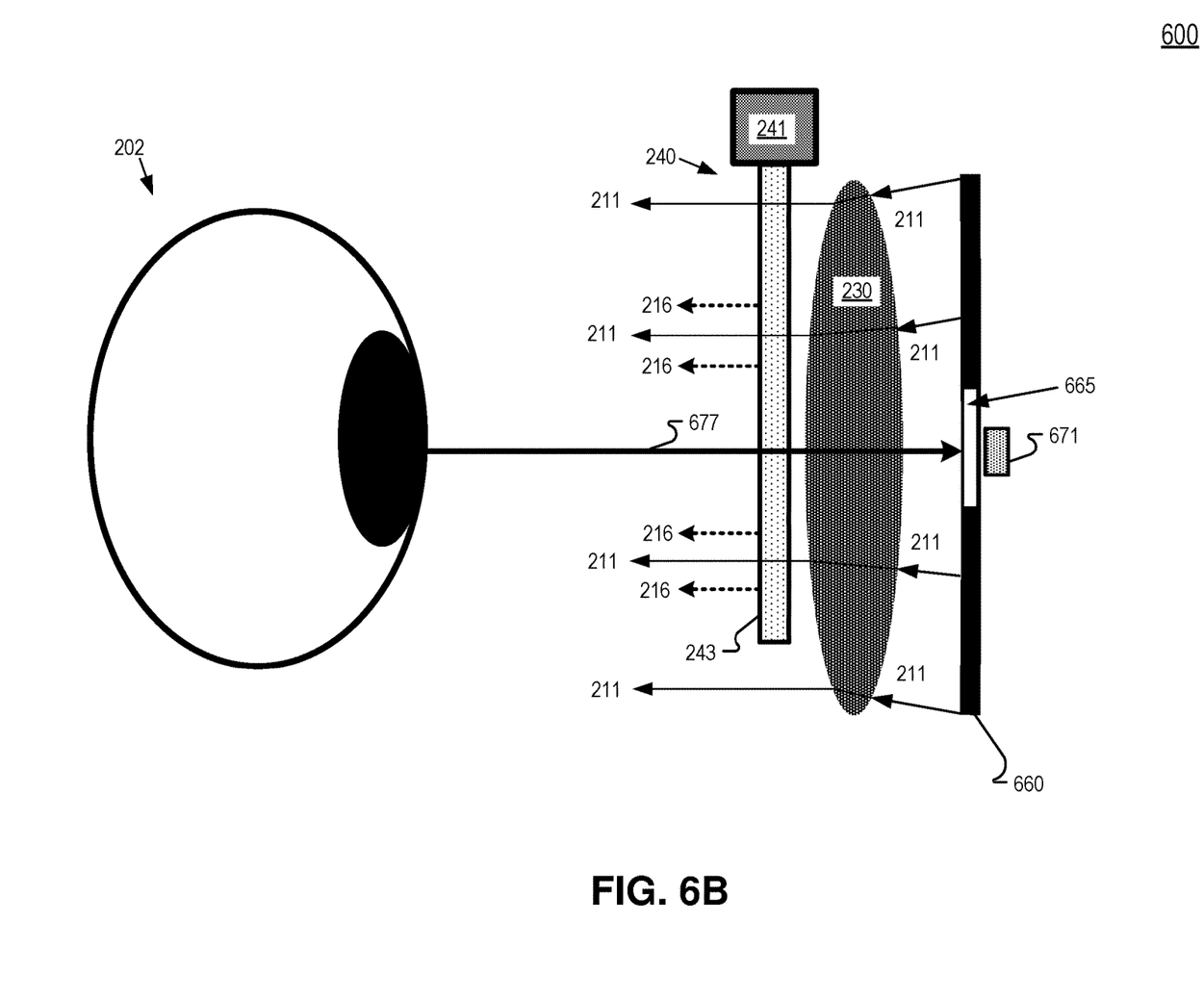

FIG. 6B illustrates an example system 600 that includes camera 671 oriented to image eye 202 through optical assembly 230 and through lightguide 243, in accordance with an embodiment of the disclosure. Camera 671 is configured to receive eye-light 677 reflecting off of eye 202. In some embodiments, eye 202 is illuminated by an infrared light source (not illustrated) and eye-light 677 is infrared light. Camera 671 may be configured to capture images of infrared light having the same wavelength as the infrared light source. Camera 671 may image the eye 202 for eye tracking purposes, in some embodiments. In this embodiment, camera 671 is behind display 660.

Figure 6C:
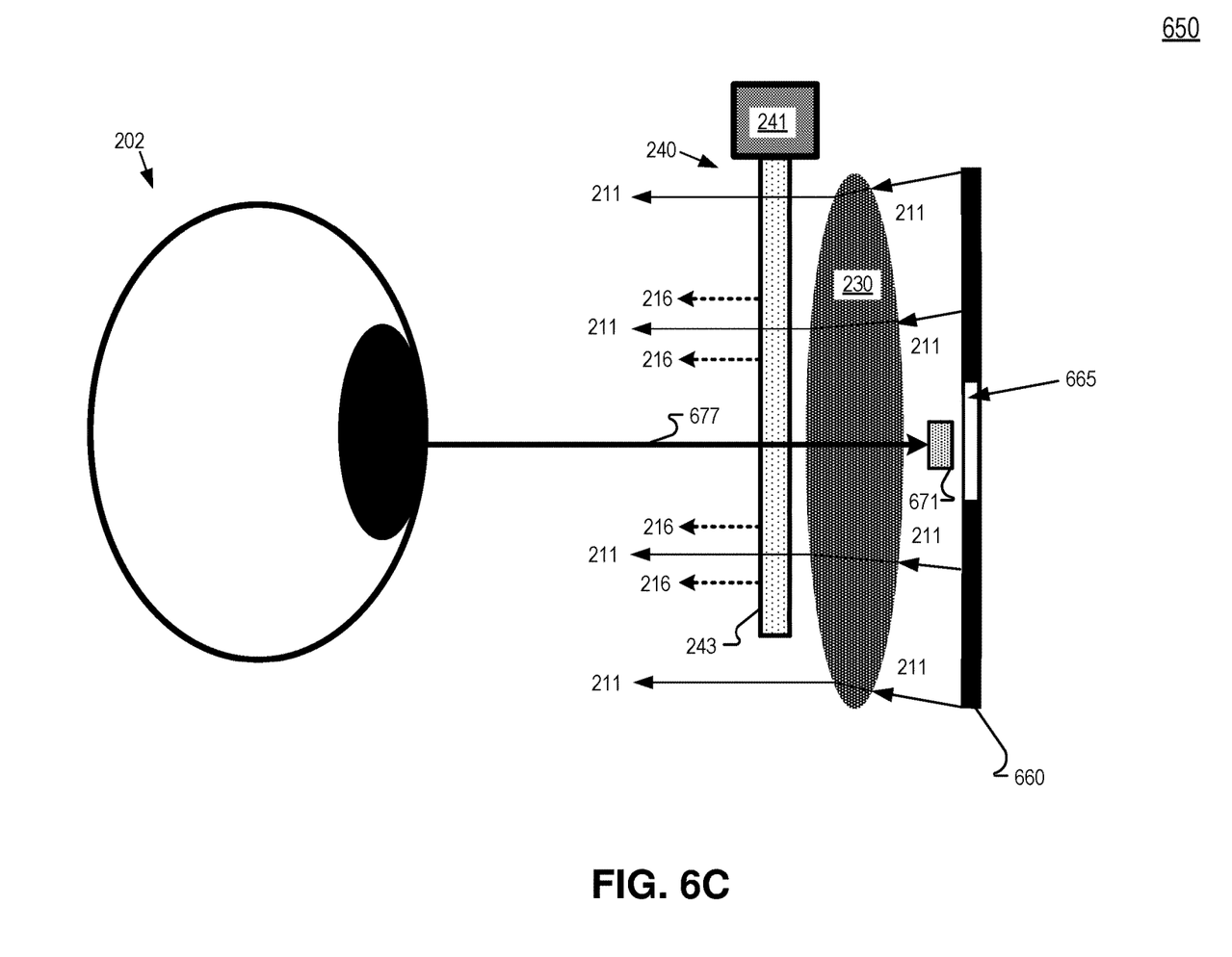

FIG. 6C illustrates an example system 650 that includes camera 671 oriented to image eye 202 through the lenses of optical assembly 230 and through lightguide 243, in accordance with an embodiment of the disclosure. In this illustrated embodiment, camera 671 is disposed between display 660 and the lenses of optical assembly 230. Camera 671 is configured to receive eye-light 677 reflecting off of eye 202. In some embodiments, eye 202 is illuminated by an infrared light source (not illustrated) and eye-light 677 is infrared light. Camera 671 may be configured to capture images of infrared light having the same wavelength as the infrared light source. Camera 671 may image the eye 202 for eye tracking purposes, in some embodiments.

Figure 7:
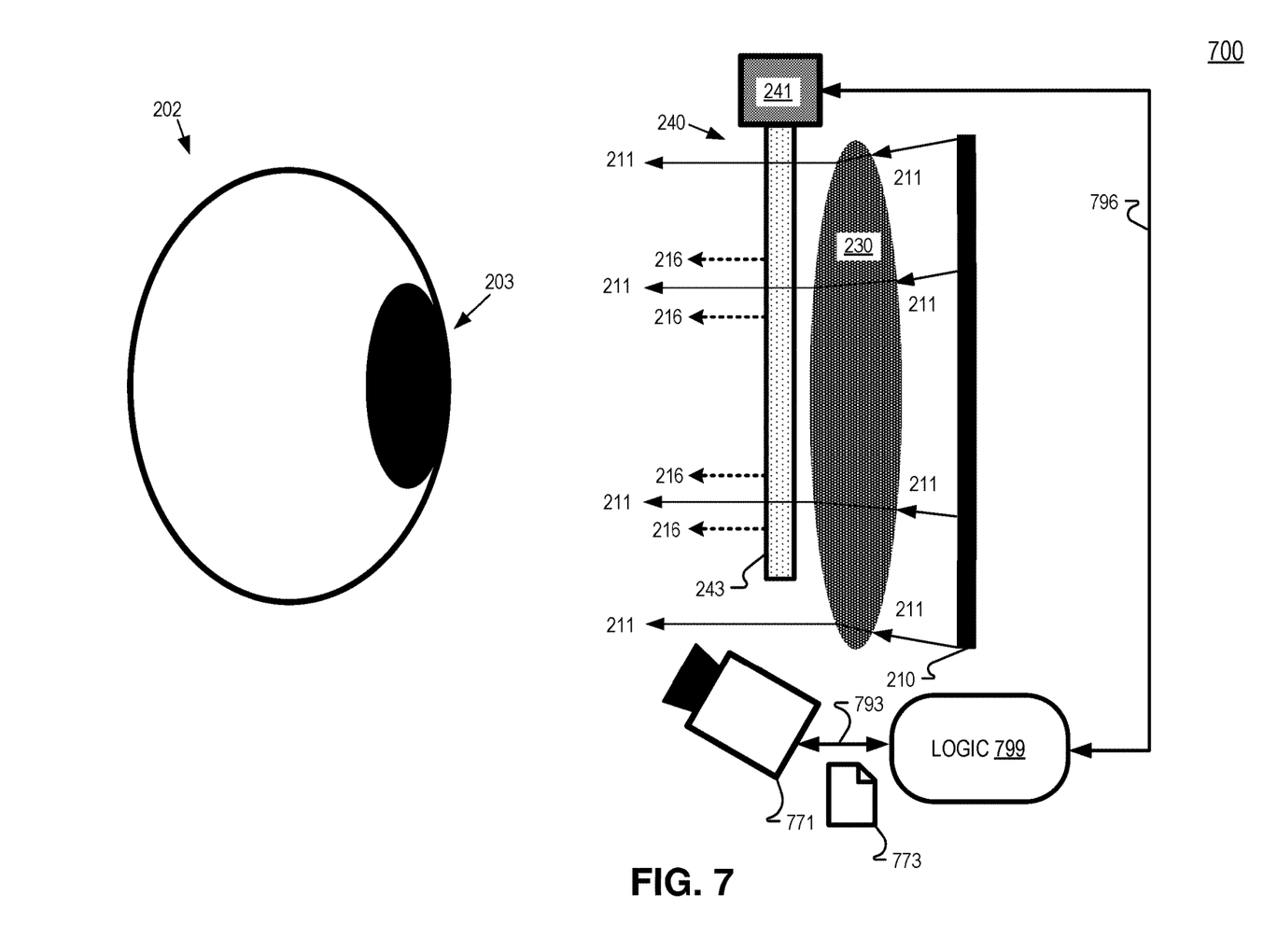
FIG. 7 illustrates a system including a camera and eye-tracking logic coupled to a display, in accordance with an embodiment of the disclosure.

FIG. 7 illustrates a system 700 including a camera and eye-tracking logic coupled to display 240, in accordance with an embodiment of the disclosure. In some embodiments, projector module 241 may include a color-sequential LCOS projector. When users perform rapid eye movements such as a saccade or rapidly tracking an object in the virtual scene, the three colors in color-sequential red/green/blue subframes may be spaced too far apart in time to produce an artifact-free image on the retina. This "color breakup" artifact is perceived as color fringing. To avoid presenting a compromised image, display 240 may be turned off in response to detecting a rapid eye movement. Since display 240 is no longer servicing the central field of view, the lower resolution display 210 is used to service the central fields with display light 211. In another embodiment, the inset display 240 may switch to a grayscale mode, where the source display (e.g. LCOS or DLP) is illuminated by all three color sources (e.g. red, green, and blue) simultaneously in response to eye-tracking logic identify a rapid eye movement by a user. The display (e.g. LCOS or DLP) continues to operate at full subframe rate. When the source display is illuminated by all three color sources simultaneously, inset display light 216 generated by display 240 is grayscale, mixing with display light 211, which may continue to operate in color or may also switch to grayscale. During the rapid eye movement, the user does not perceive "color breakup" because every subframe is presented as a grayscale image. At the end of the rapid eye movement, the display may immediately or gradually return to full-color presentation.

In system 700, camera 771 captures eye-tracking images 773 of the eye 202 of the user. Eye-tracking logic 779 is configured to receive eye-tracking images 773 from camera 771 via communication channel 793. The eye-tracking logic 799 is configured to switch off transparent display 240 in response to identify a rapid eye movement by eye 202 of the user by analyzing the eye-tracking images. The magnitude of a change in position of the pupil of eye 202 between sequential image frames may be calculated and a rapid eye movement may be defined by a pre-determined change-in-position value within a certain time period, given that the time between sequential frames is known. If the magnitude of the change in position is over the pre-determined value, for example, a rapid eye movement event may be identified. Logic 799 is configured to shut off transparent display 240 via communication channel 796, in the illustrated embodiment. In particular, eye-tracking logic 799 may deactivate projector module 241 or shut off its light source to turn transparent display 240 off. In some embodiments, transparent display 240 may be turned back on as soon as the rapid eye movement event is over. Identifying a conclusion of a rapid eye movement event may include the pupil position of pupil 203 being steady over a plurality of sequential eye-tracking images 773 that are captured subsequent to the identification of the eye-tracking event.

Figure 8:
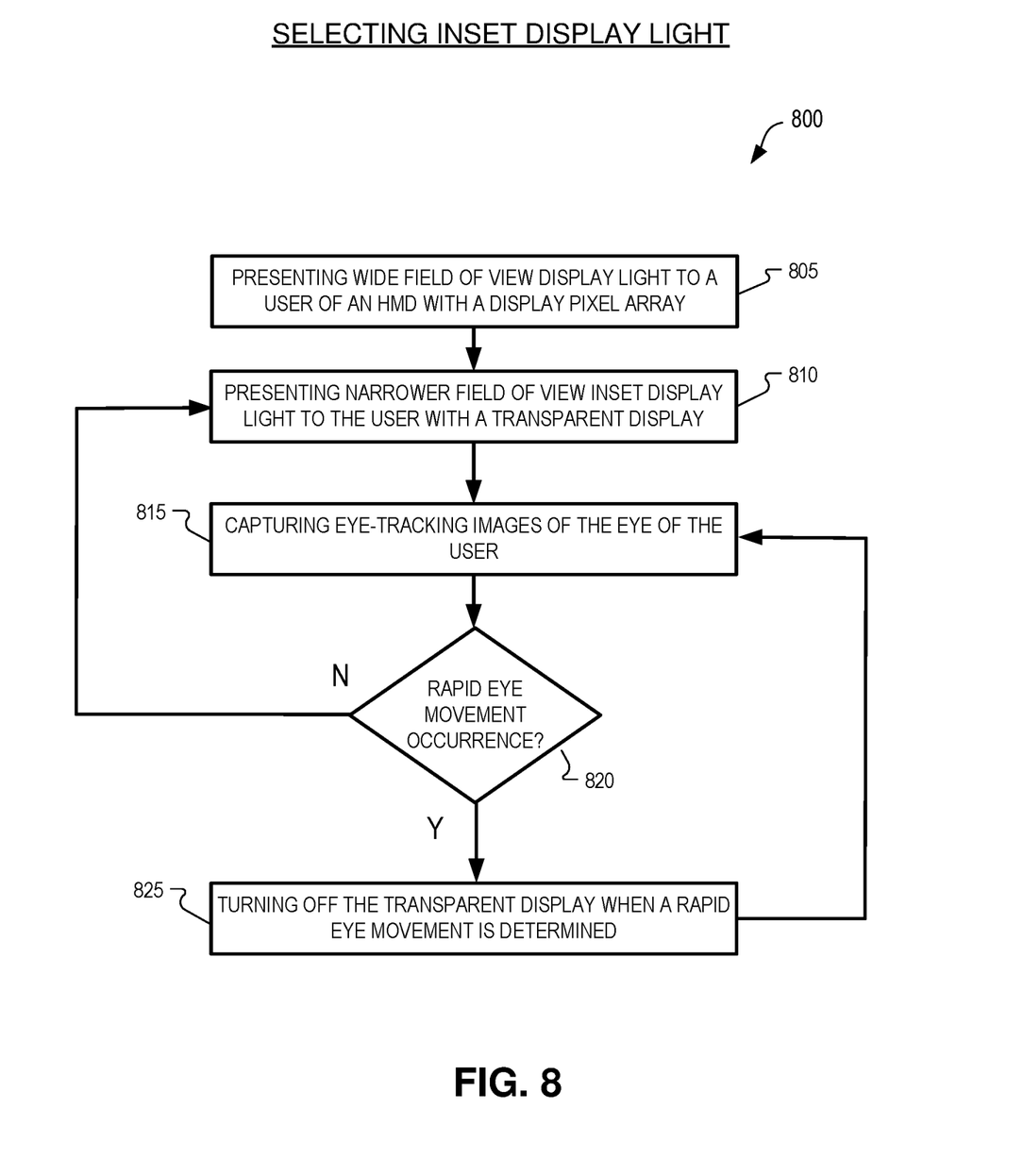
FIG. 8 illustrates a flow chart of an example process of selecting inset display light, in accordance with an embodiment of the disclosure.

FIG. 8 illustrates a flow chart of an example process 800 of selecting inset display light, in accordance with an embodiment of the disclosure. The order in which some or all of the process blocks appear in process 800 should not be deemed limiting. Rather, one of ordinary skill in the art having the benefit of the present disclosure will understand that some of the process blocks may be executed in a variety of orders not illustrated, or even in parallel.

In process block 805, display light (e.g. display light 211) is presented to a user of an HMD in a wide FOV with a display pixel array of the HMD. The display pixel array may be a non-transparent display pixel array such as found in LCD or OLED architectures.

In process block 810, inset display light (e.g. inset display light 216) is presented to the user in a FOV that is narrower than the wide FOV of the display light. The inset display light is generated by a transparent display and at least a portion of the display light propagates through the transparent display before becoming incident on an eye of the user of the HMD. The inset display light is higher resolution that the display light.

In process block 815, eye-tracking images (e.g. 773) of the eye of the user are captured. Eye-tracking images may be captured by a camera of an HMD that is oriented to image the eye.

In process block 820, the eye-tracking images are analyzed to determine whether a rapid eye movement such as a saccade has occurred. The magnitude of a change in position of the pupil of the eye between sequential image frames may be calculated and a rapid eye movement event may be defined by a pre-determined change-in-position value within a certain time period. If the magnitude of the change in position is over the pre-determined value within a pre-determined time period, for example, a rapid eye movement event may be identified. In one embodiment, the pre-determined time period is approximately 200 ms.

If no rapid eye movement occurrence is identified in process block 820, process 800 may return to process block 810. If a rapid eye movement event has been identified in process block 820, process 800 may continue to process block 825.

In process block 825, the transparent display (e.g. display 240) is turned off when the rapid eye movement is identified in process block 820. Turning off the transparent display may include turning of a light source of the display, not illuminating a display pixel array, or driving black pixel values onto the display. In one embodiment, the transparent display is turned off for a pre-determined time period in process block 825. The pre-determined time period may be between 100 ms and 500 ms, in one embodiment. After the transparent display is turned off, process 800 may return to process block 815 to capture subsequent eye-tracking images to determine whether rapid eye movement is still happening. If rapid eye movement is not still occurring (process block 820), the transparent display may be turned back on and the inset display light is again presented to the user (process block 810).

In some embodiments, transparent display 240 is always on and a portion of a FOV of the user includes higher resolution inset display light 216. The inset display light 216 may occupy a portion of the FOV of the user that is centered, upward, downward, to the side, or a combination of directions with respect to the wide FOV provided by display light 211. If there is task-based content in the images (such as a large amount of fine print text), the user can simply move her head so that the task-based content is moved to the portion of the FOV that is illuminated with the higher resolution inset display light 216. In one embodiment, a "frame" or "border" of monochrome display pixels (e.g. black) is rendered along the intersection of the display light and the inset display light so that the user can easily know where to look or move her head to view higher resolution inset display light.

Figure 9:
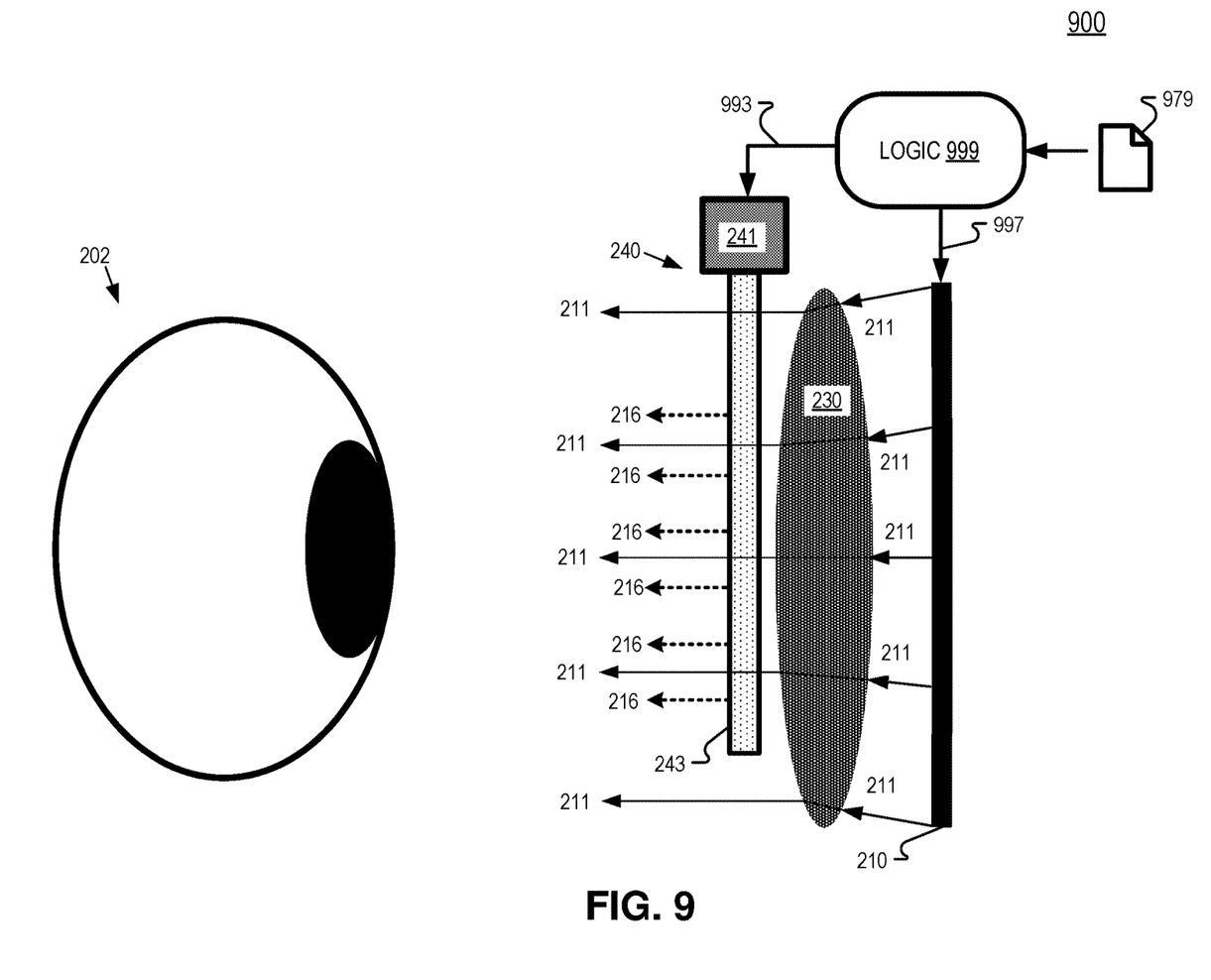
FIG. 9 illustrates a system including mode selection logic configured to activate a transparent display, in accordance with an embodiment of the disclosure.

FIG. 9 illustrates a system 900 including mode selection logic 999 configured to activate transparent display 240, in accordance with an embodiment of the disclosure. Mode selection logic 999 may activate or deactivate transparent display 240 depending on the use case of an HMD. For example, in a productivity context where a user is reading documents or charts, it may be desirable to see higher resolution images. However, in other use cases such as gaming, where rapid eye movements are common and speed is prioritized, higher resolution images for reading may be less important. Therefore, system 900 may turn transparent display 240 on and off depending on the use case.

In system 900, mode selection logic 999 may be configured to activate transparent display 240 in response to identifying text in one more images 979 to be presented to a user. Mode selection logic 999 is coupled to activate/deactivate transparent display 240 via communication channel 993, in the illustrated embodiment. Mode selection logic 999 is also configured to drive images onto display 210, in FIG. 9. If there is text in the image, it may indicate that the user will be performing a productivity task. Mode selection logic 999 may be configured to identify text in a received image 979 by performing a Fourier Transform on the received image 979 to generate a spatial frequency of the image. Based on the spatial frequency, mode selection logic 999 may determine that enough text is included in the image 979 to turn on (activate) transparent display 240. If transparent display 240 is already on and the Fourier Transform of a received image 979 (to be presented to the user) indicates there is little to no text included in the image, transparent display 240 may be turned off (deactivated).

Figure 10:
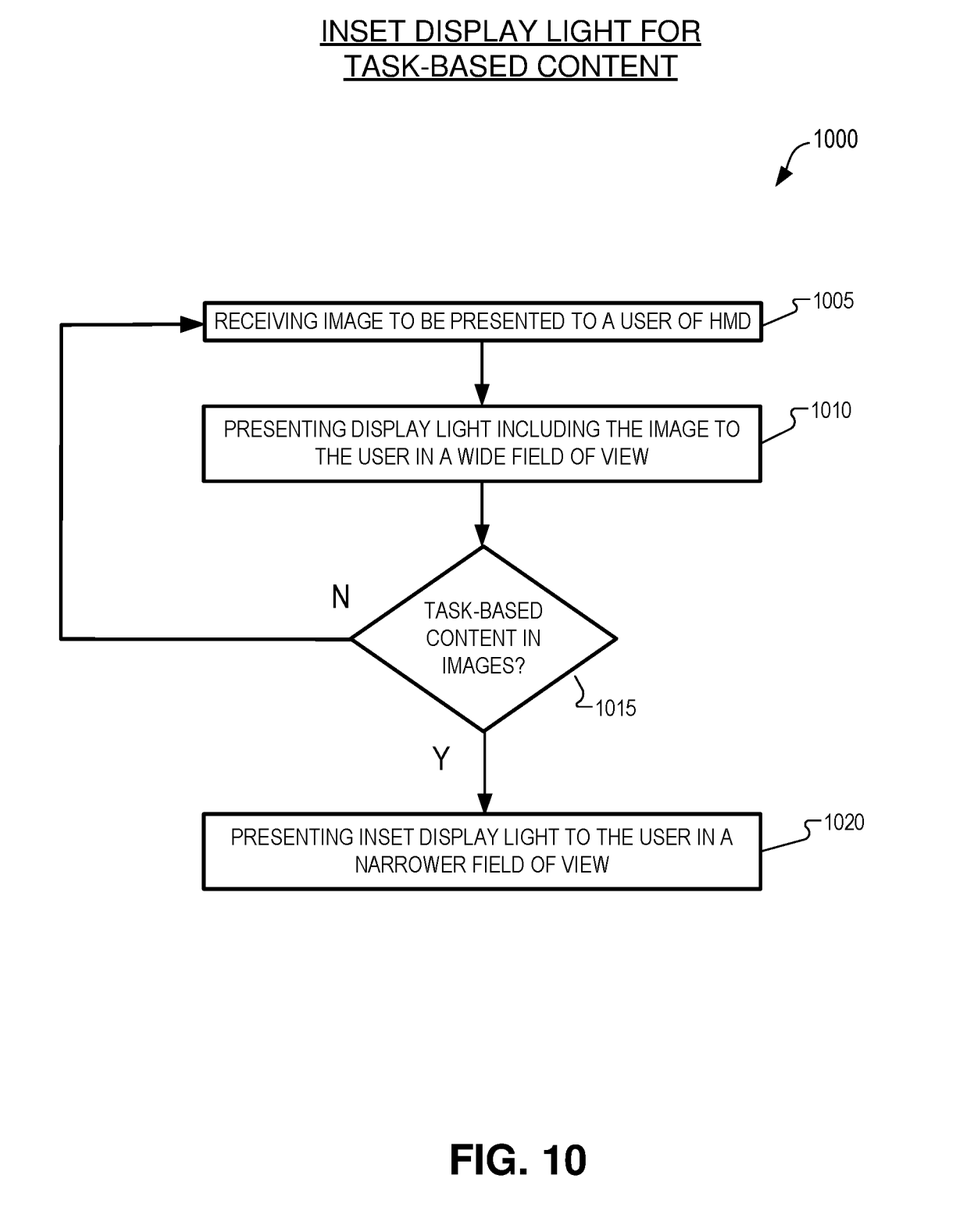
FIG. 10 illustrates a flow chart of an example process of providing inset display light for task-based content, in accordance with an embodiment of the disclosure.

FIG. 10 illustrates a flow chart of an example process 1000 of providing inset display light for task-based content, in accordance with an embodiment of the disclosure. The order in which some or all of the process blocks appear in process 1000 should not be deemed limiting. Rather, one of ordinary skill in the art having the benefit of the present disclosure will understand that some of the process blocks may be executed in a variety of orders not illustrated, or even in parallel.

In process block 1005, images (e.g. images 979) are received that will be presented to a user of an HMD. In process block 1010, display light including the images is presented to the user of the HMD in a wide FOV with a display pixel array of the HMD. The display pixel array may be included in display 210, for example.

In process block 1015, the images are analyzed to identify task-based content in the images. If task-based content is not identified, process 1000 may proceed to process block 1005. If task-based content is identified in process block 1015, process 1000 continues to process block 1020. In process block 1020, inset display light is presented to the user in a FOV that is narrower than the wide FOV of the display light (when the task-based content is identified in process block 1015). The inset display light is generated by a transparent display and at least a portion of the display light propagates through the transparent display before becoming incident on an eye of the user of the HMD. The inset display light includes at least a portion of the received image, in process block 1020. After executing process block 1020, process 1000 may return to process block 1005, in some embodiments.

Figure 11:
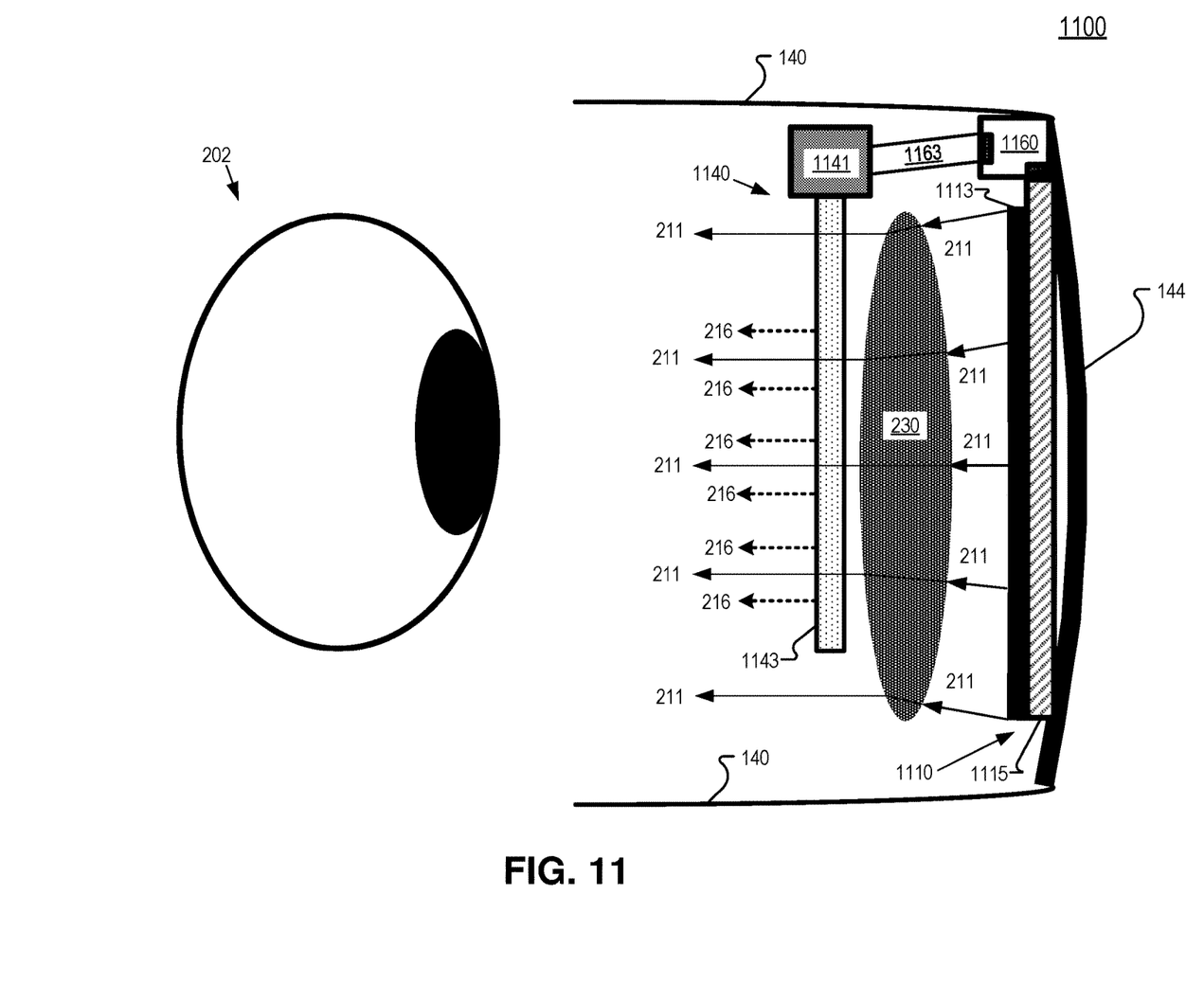
FIG. 11 illustrates a side view of a system including a non-transparent display and a transparent display that share a common light source, in accordance with an embodiment of the disclosure.

FIG. 11 illustrates a side view of a system 1100 including a non-transparent display 1110 and a transparent display 1140 that share a common light source 1160, in accordance with an embodiment of the disclosure. System 1100 may be incorporated into HMD 100, for example. Non-transparent display 1110 includes a display pixel array 1113 and a backlight unit 1115 configured to generate display light 211 that may include images for presentation to eye 202. Backlight unit 1115 is configured to illuminate non-transparent display pixel array 1113 with illumination light received from common light source 1160. Non-transparent display pixel array 1113 may include an LCD, for example. Backlight unit 1115 may be configured to evenly distribute the illumination light received from common light source 1160 to illuminate non-transparent display pixel array 1113.

Common light source 1160 provides illumination light to both non-transparent display 1110 and to transparent display 1140. In FIG. 11, common light source 1160 provides the illumination light to projector module 1141 via lightguide 1163. Where common light source 1160 includes more than one light source (e.g. red, green, and blue LED(s)), lightguide 1163 may be of a sufficient mixing distance to mix the multiple colors of light source into white light. Common light source 1160 may provide RGB illumination light to an LCOS-based transparent display 1140 while also providing RGB illumination light to an LCD-based architecture of non-transparent display 1110.

Having common light source 1160 provide illumination light to both transparent display 1140 and non-transparent display 1110 assists in brightness matching and color matching over the lifetime of displays 1110 and 1140. LEDs used as light sources typically experience brightness degradation and wavelength-shift over the lifetime of the LED(s). Wavelength-shift can be particularly acute in red LEDs and wavelength-shift in any LED affects the color of the displayed images. LEDs in common light source 1160 may also change brightness and color but the changes in the brightness and color of displays 1110 and 1140 will be evenly matched since common light source 1160 provides illumination light to both displays 1110 and 1140.

Embodiments of the invention may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The term logic (e.g. 799 or 999) in this disclosure may include one or more processors, microprocessors, multi-core processors, Application-specific integrated circuits (ASIC), and/or Field Programmable Gate Arrays (FPGAs) to execute operations disclosed herein. In some embodiments, memories (not illustrated) are integrated into the processing logic to store instructions to execute operations and/or store data. Processing logic may also include analog or digital circuitry to perform the operations in accordance with embodiments of the disclosure.

A "memory" or "memories" described in this disclosure may include one or more volatile or non-volatile memory architectures. The "memory" or "memories" may be removable and non-removable media implemented in any method or technology for storage of information such as computer-readable instructions, data structures, program modules, or other data. Example memory technologies may include RAM, ROM, EEPROM, flash memory, CD-ROM, digital versatile disks (DVD), high-definition multimedia/data storage disks, or other optical storage, magnetic cassettes, magnetic tape, magnetic disk storage or other magnetic storage devices, or any other non-transmission medium that can be used to store information for access by a computing device.

Communication channels 793, 796, 993 and/or 997 may include or be routed through one or more wired or wireless communication utilizing IEEE 802.11 protocols, BlueTooth, SPI (Serial Peripheral Interface), I$^2$C (Inter-Integrated Circuit), USB (Universal Serial Port), CAN (Controller Area Network), cellular data protocols (e.g. 3G, 4G, LTE, 5G), optical communication networks, Internet Service Providers (ISPs), a peer-to-peer network, a Local Area Network (LAN), a Wide Area Network (WAN), a public network (e.g. "the Internet"), a private network, a satellite network, or otherwise.

A computing device may include a desktop computer, a laptop computer, a tablet, a phablet, a smartphone, a feature phone, a server computer, or otherwise. A server computer may be located remotely in a data center or be stored locally.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A Head Mounted Display (HMD) comprising:
   a non-transparent display pixel array for providing display light;
   a collimating lens configured to provide the display light to a user of the HMD in a wide field of view;
   a transparent display configured to provide inset display light having a field of view narrower than the wide field of view, wherein at least a portion of the display light propagates through the transparent display before becoming encountering an eyebox area;
   a camera; and
   eye-tracking logic configured to receive eye-tracking images from the camera, wherein the eye-tracking logic is configured to switch off the transparent display in response to identifying a rapid eye movement by analyzing the eye-tracking images.

2. The HMD of claim 1, wherein the transparent display includes a lightguide that directs the inset display light to the eyebox area.

3. The HMD of claim 2, wherein the lightguide includes a light input end and a plurality of partially mirrored surfaces that get progressively more reflective as the partially mirrored surfaces get farther from the light input end of the lightguide, the plurality of partially mirrored surfaces configured to direct the inset display light to the eyebox area.

4. The HMD of claim 2, wherein the lightguide include diffraction structures to direct the inset display light to the eyebox area.

5. The HMD of claim 2, wherein the transparent display includes a liquid crystal on silicon (LCOS) projector configured to illuminate the lightguide with projected light.

6. The HMD of claim 1, wherein the
   camera is oriented to image the eyebox area through the collimating lens, wherein the non-transparent display pixel array includes a pixel void region surrounded by display pixels of the non-transparent display pixel array, and wherein the camera is disposed in the pixel void region.

7. The HMD of claim 6, wherein the pixel void region is in a portion of the wide field of view that is illuminated by the inset display light.

8. The HMD of claim 1 further comprising:
   mode selection logic configured to activate the transparent display in response to identifying text in an image being presented to the user.

9. The HMD of claim 8, wherein identifying text in the image includes performing a Fourier Transform on the image to generate a spatial frequency image.

10. The HMD of claim 1, wherein the wide field of view exceeds 100 degrees horizontal, and wherein the field of view of the transparent display exceeds 50 degrees horizontal.

11. The HMD of claim 1, wherein the non-transparent display pixel array includes a liquid crystal display pixel array, and wherein the transparent display includes a liquid crystal on silicon (LCOS) projector.

12. The HMD of claim 1, wherein the collimating lens provides an effective focal length of between 20 mm and 30 mm.

13. The HMD of claim 1, wherein inset display light is higher resolution than the display light.

14. The HMD of claim 1 further comprising:
    a common light source configured to provide illumination light to the transparent display; and
    a backlight unit configured to illuminate the non-transparent display pixel array with the illumination light received from the common light source.

15. A computer-implemented method comprising:
    receiving images to be presented to a user of a head mounted display (HMD);
    presenting display light including the images to the user of the HMD in a wide field of view with a display pixel array of the HMD;
    analyzing the images to identify task-based content in the images; and
    presenting inset display light to the user in a field of viewer narrower than the wide field of view when the task-based content is identified in the images, wherein identifying task-based content includes identifying text in the images being presented to the user, wherein the inset display light is generated by a transparent display, and wherein at least a portion of the display light propagates through the transparent display before encountering an eyebox area.

16. The computer-implemented method of claim 15, wherein identifying text in the images includes performing a Fourier Transform on the images to generate a spatial frequency image.

17. The computer-implemented method of claim 15 further comprising:
    rendering a frame along an intersection of the display light and the inset display light, wherein the inset display light is higher resolution than the display light.

18. A computer-implemented method comprising:
    presenting display light to a user of a head mounted display (HMD) in a wide field of view with a display pixel array of the HMD;
    presenting inset display light to the user in a field of viewer narrower than the wide field of view, wherein the inset display light is generated by a transparent display, and wherein at least a portion of the display light propagates through the transparent display before becoming incident on an eye of the user of the HMD;
    capturing eye-tracking images of the eye of the user;
    analyzing the eye-tracking images to determine whether a rapid eye movement has occurred; and
    turning off the transparent display when the rapid eye movement is determined.

19. The computer-implemented method of claim 18, wherein the inset display light is higher resolution than the display light.

* * * * *